Figure 1:
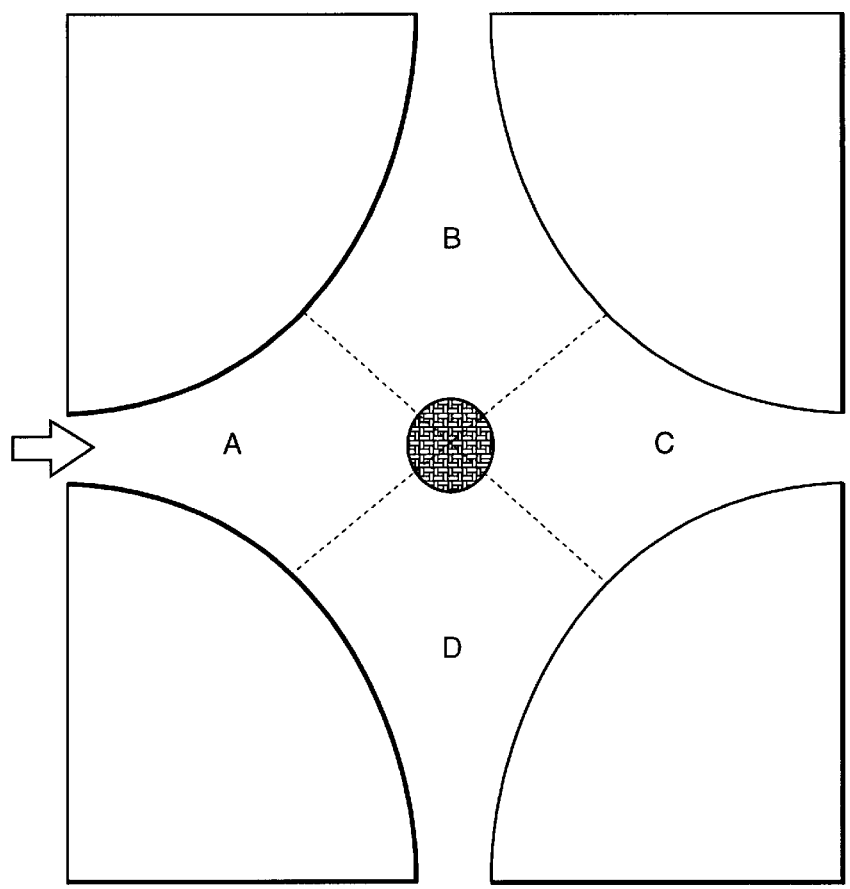

US005770189A

United States Patent [19]
Airey et al.

[11] Patent Number: 5,770,189
[45] Date of Patent: Jun. 23, 1998

[54] USE OF DIBUTYL MALATE AS INSECT ATTRACTANT

[75] Inventors: Michael John Airey, Blackburn; Angela Janousek, Canterbury, both of Great Britain; Erich Klein, Graz, Austria; Stephen David Watkins, Ashford, Great Britain

[73] Assignee: Quest International B.V., Naarden, Netherlands

[21] Appl. No.: 765,068

[22] PCT Filed: Jul. 5, 1995

[86] PCT No.: PCT/EP95/02614

§ 371 Date: Mar. 27, 1997

§ 102(e) Date: Mar. 27, 1997

[87] PCT Pub. No.: WO96/01052

PCT Pub. Date: Jan. 18, 1996

[30] Foreign Application Priority Data

Jul. 6, 1994 [EP] European Pat. Off. .............. 94304965

[51] Int. Cl.⁶ ............................. A01N 37/06; A01M 1/14; A01M 1/20; A01M 1/22

[52] U.S. Cl. ............................. 424/84; 424/405; 424/409; 514/547; 43/107; 43/132.1

[58] Field of Search ............................. 424/84, 405, 409; 514/547; 43/107, 112, 114, 124, 131, 132.1, 133, 134, 136

[56] References Cited

PUBLICATIONS

Svirbely, W.J. et al., "Physical Properties of Some Organic Insect Repellents," The Journal of the American Chemical Society, vol. 71, 1949, pp. 507–509.

Primary Examiner—John Pak
Attorney, Agent, or Firm—Cushman Darby & Cushman Intellectual Property Group of Pillsbury Madison & Sutro LLP

[57] ABSTRACT

The invention relates to the use of dibutyl malate as an attractant for domestically occurring flies, particularly of the species Musca domestica and Fannia canicularis, and to insect traps characterized by emanating dibutyl malate vapors. Preferably the dibutyl malate is diluted before evaporation with a liquid diluent or a solid diluent or carrier such that the concentration in or on the trap is below 10% by weight.

8 Claims, 2 Drawing Sheets

USE OF DIBUTYL MALATE AS INSECT ATTRACTANT

This application is the national phase of international application PCT/EP95/02614 filed Jul. 5, 1995 published as WO96/01052 Jan. 18, 1996, which designated the U.S.

The present invention relates to the use of dibutyl malate as an attractant for certain insects and to insect attracting devices intended for trapping or killing flies comprising dibutyl malate as an attractant. Particularly, the invention concerns the use of dibutyl malate for attracting domestically occuring flies such as the housefly (Musca domestica) and the lesser housefly (Fannia canicularis). Furthermore the invention concerns a method for catching flies using dibutyl malate as an attractant.

Although most domestically occuring flies, like the common house fly, do not present a direct nuisance or health hazard to the human body, as do biting or stinging insects, they do present a hygiene problem in that they may infect food with pathogenic microorganisms and thus accelerate food spoilage. Therefore there is a need for combatting flies in environments where food is stored or prepared. Moreover, many people consider flies a nuisance in their homes. Compounds which are able to attract flies can play an import role in combatting them by luring them into traps where they are killed or immobilized.

Various compounds and compositions attracting house flies, often together with other insects, have been described in U.S. Pat. Nos. 4,764,367, 4,801,446, 4,801,448, 4,808,403, 4,859,463, 4,880,625, 4,911,906, 4,959,209, 4,988,507 and 4,988,508. One of the compounds mentioned is dibutyl succinate, but this appears to be an attractant for other insects than Musca domestica.

The insect attractant properties of a large number of compounds for ten different insect species have been compiled by M. Beroza and N. Green and described in Agriculture Handbook No. 239, published in 1963 by the Agricultural Research Service of The USA Department of Agriculture. Several esters of malic acid were reported to be slightly attractive to various fruit flies, Gypsy moth and Drosophila; no data for the house fly were reported.

On the other hand dibutyl malate and various other malate esters were reported as effective repellents against:
various biting insects, U.S. Pat. No. 4,047,505;
biting midges, Mosq. News, 43(3) 1983, 338–342;
yellow fever mosquitoes, J. Econ. Entomol. 60(6) 1967, 1587–1590;
black flies, J. Econ. Entomol. 44 1951, 813–814;
sand flies, Proc. New Jersey Mosquito Exterm. Assoc. 37 1950, 154–156;
tsetse fly, Trans. Royal Soc. Trop. Med. Hyg. 40(3) 1946, 341–344.

Furthermore, dibutyl malate was reported as an effective insect repellent in J. Am. Chem. Soc. 71 1949, 507–509.

Finally malic acid (but not any malate ester) is mentioned as a component of an insect attractant composition in Japanese Patent Appln No. 54.095732.

It has now been found that dibutyl malate is a powerful attractant for domestically occuring flies, more particularly the housefly (Musca domestica) and the lesser housefly (Fannia canicularis), and thus can be used in a method for catching flies by luring them into or onto an insect attracting device or insect trap. The compound can be used for this purpose, either as such or in combination with other insect attracting substances. Therefore, insect attracting devices or traps according to the invention are characterized by emanating dibutyl malate vapors, thus causing a concentration gradient of dibutyl malate in the atmosphere surrounding them which will lure the flies into or onto the trap. Conventionally such traps also comprise means for killing or immobilizing the flies e.g. a toxic substance with which the fly is brought into contact, a tacky surface from which the fly cannot escape once it has landed thereon, some electric killing device or any other killing or immobilizing means known in the art. Furthermore traps intended for domestically occuring flies are generally specifically designed for trapping flying insects, e.g. by providing a means for hanging them from a ceiling, and are generally used indoors.

Dibutyl malate is a liquid at room temperature. It is substantially insoluble in water but soluble in isopropanol, diethyl ether, hexane and other low polar or non-polar organic solvents.

Preferably the dibutyl malate is diluted, either after evaporation from the trap by adding a gaseous diluent such as air, or before evaporation from the trap by mixing with a liquid or solid diluent. In the latter case the concentration of dibutyl malate in or on the trap is preferably below 10% by weight, more preferably between 5 and 0.0001%. The optimum concentration for a specific kind of application depends on the diluent used and the construction of the trap and can be determined by simple experimentation with a range of concentrations.

A suitable liquid diluent may be water, in which dibutyl malate may be dispersed using some conventional dispersing means such as an emulsifier, or it may be an organic liquid such as those mentioned above or mineral oil, polyethylene glycol, vegetable oil, parrafin, a resinous material or the like. Solid diluents or carriers may be wood, paper, textile, porous organic polymers or inorganic absorbent media such as zeolites, silica, activated carbon, aluminium oxide and the like from which dibutyl malate can evaporate at a desired rate.

The fly-attracting properties of dibutyl malate are illustrated in the examples below:

EXAMPLE 1

The attracting properties of dibutyl malate were tested using the olfactometer made of transparent perspex as depicted in FIG. 1. The exposure chamber has the shape of a four-pointed star, with an inlet tube at each point of the star. Gases are sucked into the exposure chamber through the inlet tubes and drawn out by a pump connected to an opening in the centre of its floor. The shape of the exposure chamber with its curved walls prevents the four air flows from mingling and creates sharp borderlines between the adjacent fields (indicated in FIG. 1 by A, B, C and D). The olfactometer was placed in a room kept at 22°±2° C. and constant relative humidity. No daylight could enter the room and it was lit by fluorescent tubes. The flies used in this test were of the species Fannia canicularis.

Figure 2:
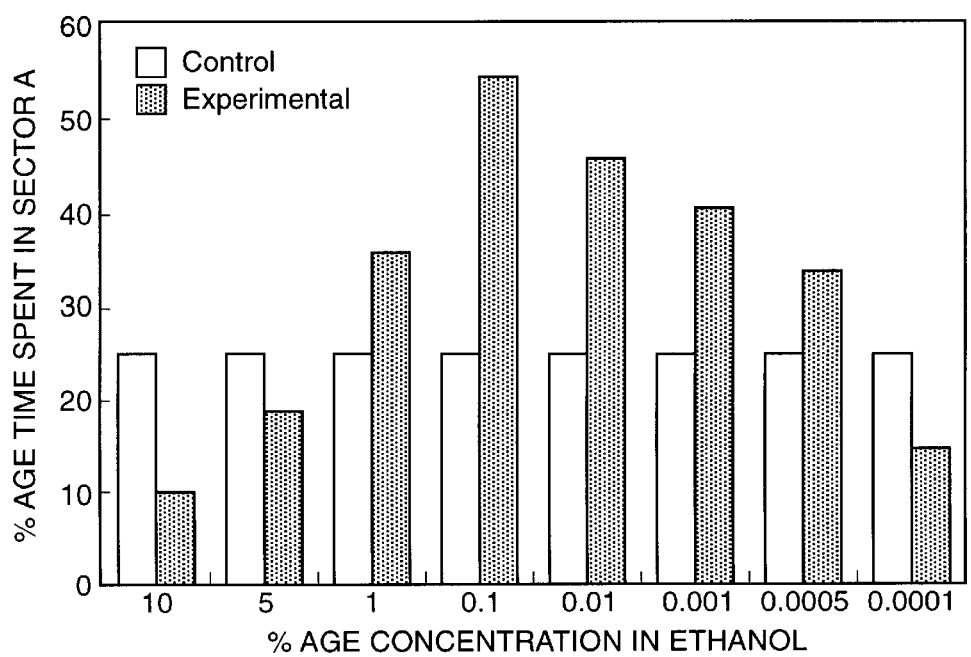

A test tube containing a solution of dibutyl malate in ethanol was attached to inlet tube A such that the air sucked in via this tube carried the dibutyl malate vapors with it. Identical test tubes with pure ethanol were attached to the other inlet tubes. A fly was placed at the centre of the exposure chamber and allowed to acclimate for 5 minutes whereafter the air flows were sucked into the chamber. The position of the fly was recorded at 30 second intervals for 10 minutes. The percentage of time that the fly spent in sector A was calculated. The experiment was repeated with different concentrations of dibutyl malate and for each concentration with 10 flies. The results are presented as a bar graph in FIG. 2, which clearly shows that dibutyl malate clearly acts as a fly-attractant at concentrations between 1 and 0.0005% in ethanol.

EXAMPLE 2

This experiment was carried out in the same room as used in Example 1.

A volume of 2 ml of a solution of dibutyl malate in 70% aqueous ethanol was mixed with enough Aerosil 200* to form a paste. This paste was applied to the top of a 25 cm×10 cm sheet of yellow card. This coloured card was chosen because in other tests this particular shade of yellow proved to be attractive to Fannia canicularis. The yellow cards were previously coated with a clear odourless glue. The yellow baited target card was hung at one end of a tank (120 cm×38 cm ×30 cm) and the tank sealed. 20 flies of the species Fannia canicularis were released at the other end of the tank and thereafter the tank remained sealed for 18 hours, after which the number of flies stuck to the card was recorded.

* Trademark of Degussa, Germany

Figure 3:
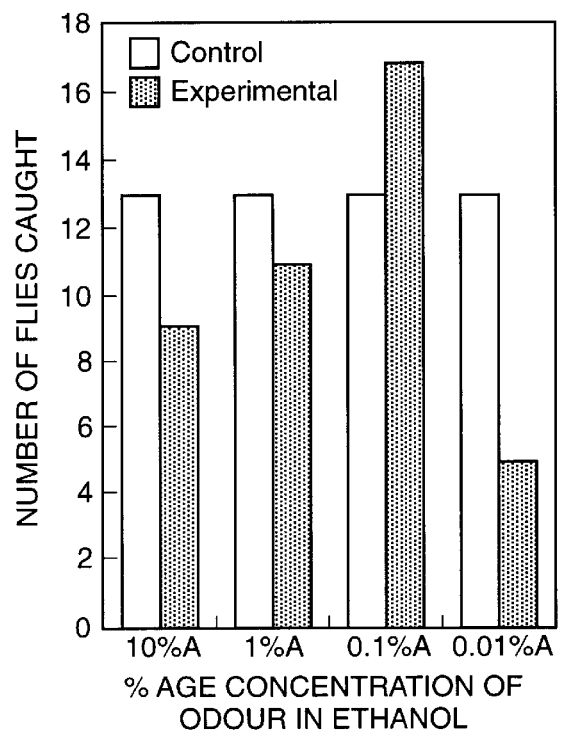

The test was repeated with four different concentrations of dibutyl malate and with pure 70% aqueous ethanol as a control. The results are presented as a bar graph in FIG. 3, from which it can be seen that in this experiment dibutyl malate at a concentration of 0.1% lured significantly more flies to the target than the control, and that the attractancy is concentration dependent.

EXAMPLE 3

In this experiment the same room was used as in Examples 1 and 2 and the same yellow cards prepared in the same way as in Example 2. The flies used were of the species Musca domestica and Fannia canicularis.

Figure 4:
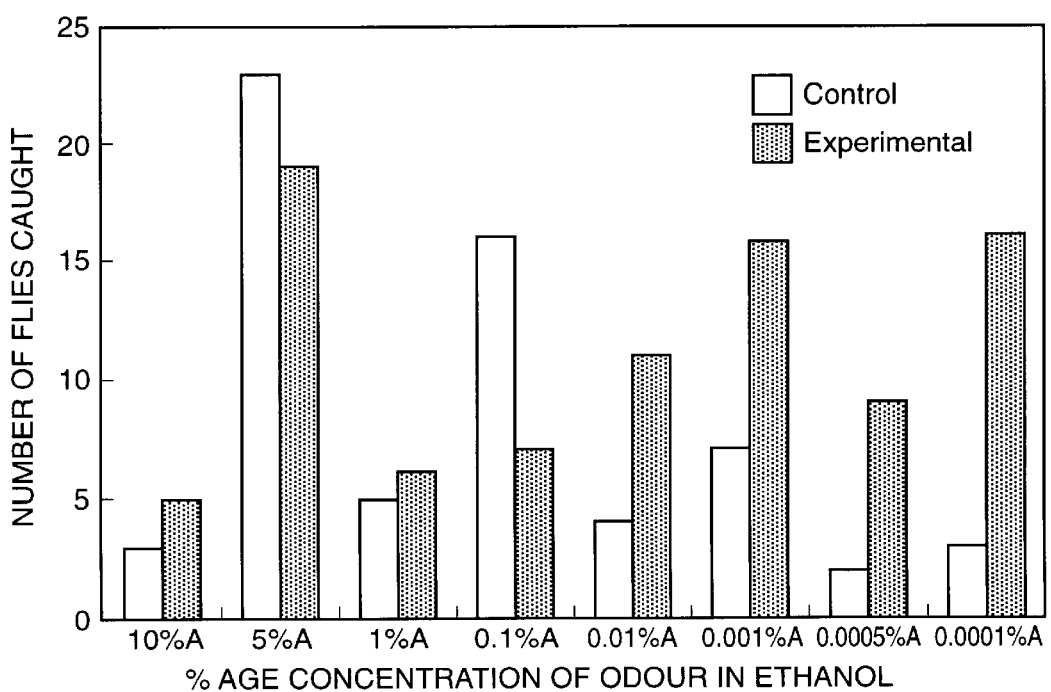

A baited target card was hung from the ceiling of the room for each test while at the same time a control card, also treated as the control card in Example 2, was hung from the ceiling. An undetermined number of flies were released in the room. The room was kept closed for 4 hours, whereafter the number of flies on the baited card and the control card was counted. The results are presented in FIG. 4.

We claim:

1. An insect trap for domestically ocurring flies comprising means for emanating dibutyl malate vapors to the surrounding atmosphere and means for killing or immobilizing the flies.

2. An insect trap according to claim 1 wherein the fly killing or immobilizing means comprises a toxic substance, a sticky substance or an electric killing device.

3. A method for catching domestically occurring flies which comprises exposing said flies to dibutyl malate vapors emanating from an insect trap thereby causing a concentration gradient of dibutyl malate in the atmosphere surrounding the flies which will lure the flies into or onto the trap.

4. A method according to claim 3 wherein the flies belong to the species Musca domestica and Fannia canicularis.

5. A method according to claim 3 or 4 wherein the dibutyl malate is diluted with a gaseous, liquid or solid diluent.

6. A method according to claim 5 wherein the dibutyl malate is diluted before evaporation with a liquid diluent or a solid diluent or carrier.

7. A method according to claim 6 wherein the concentration of dibutyl malate in or on the trap is below 10% by weight.

8. A method according to claim 7 wherein the concentration of dibutyl malate is between 5 and 0.0001% by weight.

* * * * *